(12) United States Patent
Receveur et al.

(10) Patent No.: US 12,097,154 B2
(45) Date of Patent: Sep. 24, 2024

(54) UNIVERSAL LOAD CELL FEATURES THAT CHARACTERIZE PATIENT MOTION IN THREE DIMENSIONS IN A HOSPITAL BED

(71) Applicant: Hill-Rom Services, Inc., Batesville, IN (US)

(72) Inventors: Timothy J. Receveur, Batesville, IN (US); Hyeon Ki Jeong, Atlanta, GA (US); Daniel M. Hochman, Atlanta, GA (US)

(73) Assignee: Hill-Rom Services, Inc., Batesville, IN (US)

( * ) Notice: Subject to any disclaimer, the term of this patent is extended or adjusted under 35 U.S.C. 154(b) by 210 days.

(21) Appl. No.: 17/676,308

(22) Filed: Feb. 21, 2022

(65) Prior Publication Data
US 2022/0273509 A1 Sep. 1, 2022

Related U.S. Application Data

(60) Provisional application No. 63/154,055, filed on Feb. 26, 2021.

(51) Int. Cl.
 *A61G 7/00* (2006.01)
 *A61G 7/05* (2006.01)
(52) U.S. Cl.
 CPC ........ *A61G 7/0527* (2016.11); *A61G 2203/32* (2013.01); *A61G 2203/36* (2013.01)
(58) Field of Classification Search
 CPC .......... A61G 7/00; A61G 7/05; A61G 7/0527; A61G 2203/32; A61G 2203/36
 See application file for complete search history.

(56) References Cited

U.S. PATENT DOCUMENTS

| | | |
|---|---|---|
| 8,350,709 B2 | 1/2013 | Receveur |
| 8,432,287 B2 | 4/2013 | O'Keefe et al. |
| 8,437,876 B2 | 5/2013 | Receveur et al. |
| 8,525,679 B2 | 9/2013 | Riley et al. |
| 8,525,680 B2 | 9/2013 | Riley et al. |
| 9,013,315 B2 | 4/2015 | Riley et al. |
| 9,044,204 B2 | 6/2015 | Riley et al. |
| 9,295,600 B2 | 3/2016 | Receveur |
| 9,383,250 B2 | 7/2016 | Receveur et al. |
| 9,549,675 B2 | 1/2017 | Riley et al. |
| 9,549,705 B2 | 1/2017 | Riley et al. |

(Continued)

FOREIGN PATENT DOCUMENTS

EP 3912609 A1 11/2021

OTHER PUBLICATIONS

European Search Report in related EPO Application No. 22158232.3 1126 dated Jul. 15, 2022, 9 pages.

*Primary Examiner* — Fredrick C Conley
(74) *Attorney, Agent, or Firm* — Barnes & Thornburg LLP

(57) ABSTRACT

A patient support apparatus comprise a first frame, a plurality of load cells positioned on the first frame, a second frame, and a control system. The control system includes a controller, the controller is operable to receive a separate signal from each of the plurality of load cells, process the signals to identify, based on transient changes in the forces measured by each of the plurality of load cells, motion of the patient, classify the motion of the patient, and, based on the classification, update a patient profile in a patient record to reflect the characterization of the patient motion.

20 Claims, 8 Drawing Sheets

(56) References Cited

U.S. PATENT DOCUMENTS

| | | | |
|---|---|---|---|
| 9,552,460 B2 | 1/2017 | Riley et al. | |
| 9,775,758 B2 | 10/2017 | Riley et al. | |
| 9,782,108 B2 | 10/2017 | Shimizu | |
| 10,111,794 B2 | 10/2018 | Riley et al. | |
| 10,219,725 B2 | 3/2019 | Williamson et al. | |
| 10,297,143 B1 | 5/2019 | Giffen et al. | |
| 10,363,181 B2 | 7/2019 | Williamson et al. | |
| 10,583,058 B2 | 3/2020 | Riley et al. | |
| 10,588,802 B2 | 3/2020 | Wiggermann et al. | |
| 10,786,408 B2 * | 9/2020 | Sidhu | A61G 7/018 |
| 11,081,221 B2 | 8/2021 | Huster et al. | |
| 2009/0119843 A1 * | 5/2009 | Rodgers | G16Z 99/00 |
| | | | 705/3 |
| 2011/0030141 A1 * | 2/2011 | Soderberg | A61M 5/172 |
| | | | 5/600 |
| 2012/0259245 A1 | 10/2012 | Receveur | |
| 2013/0229283 A1 | 9/2013 | Receveur et al. | |
| 2013/0267791 A1 * | 10/2013 | Halperin | A61B 5/6891 |
| | | | 600/300 |
| 2014/0066815 A1 | 3/2014 | Williamson et al. | |
| 2014/0124273 A1 * | 5/2014 | Receveur | G01G 19/445 |
| | | | 177/7 |
| 2014/0352060 A1 * | 12/2014 | Hirose | A47C 19/02 |
| | | | 5/310 |
| 2016/0106345 A1 | 4/2016 | Kostic et al. | |
| 2017/0224253 A1 | 8/2017 | Berlin et al. | |
| 2017/0296103 A1 * | 10/2017 | Ojha | A47G 9/1045 |
| 2019/0053707 A1 * | 2/2019 | Lane | G16H 40/67 |
| 2019/0183427 A1 | 6/2019 | Fu et al. | |
| 2019/0266870 A1 | 8/2019 | Zhao et al. | |
| 2020/0110194 A1 | 4/2020 | Young et al. | |
| 2021/0202091 A1 | 7/2021 | Receveur et al. | |
| 2021/0298683 A1 | 9/2021 | Jung et al. | |
| 2021/0338167 A1 | 11/2021 | Receveur et al. | |

* cited by examiner

UNIVERSAL LOAD CELL FEATURES THAT CHARACTERIZE PATIENT MOTION IN THREE DIMENSIONS IN A HOSPITAL BED

PRIORITY CLAIM

This application claims priority under 35 U.S.C. § 119(e) to U.S. Provisional Application No. 63/154,055, filed Feb. 26, 2021, which is expressly incorporated by reference herein.

BACKGROUND

The present disclosure relates to the use of load cells of a scale system of a patient support apparatus for characterizing patient motion. More specifically, the present disclosure relates to using the load cells of the scale system to characterize patient motion in three dimensions.

The use of load cells in patient support apparatuses, such as hospital beds, for example, to measure patient weight is known. Over time, approaches to using the information from the load cells to detect patient movement and to issue an alert or notification when the patient moves beyond a particular threshold have been developed. The use of load cells to make these determinations and inferences based on the motion is limited by the potential for external influences, such as the addition of equipment to the frame supported on the scale. When this is done, the existing information regarding the position of the patient is compromised as the weight distribution is changed unexpectedly.

In addition, caregivers or visitors may intermittently apply pressure to the frame, thereby changing weight measurements and the distribution of the weigh on the frame. Motion algorithms generally rely on changes the distribution of weight over multiple sensors to determine patient location and relative movement. These transient and external forces confound the algorithms used to determine patient movement and motion.

In some cases, it is important to determine patient movement relative to the patient support apparatus. Movement in this context means a change in position of the patient on the patient support apparatus, such as rolling over or moving toward an edge of a patient support apparatus to exit the patient support apparatus, for example. In other cases, it is important to identify patient motion such as movement of limbs or oscillating motion that does not result in a change of position or movement of the patient relative to the patient support apparatus, but is still useful in predicting patient outcomes or potential future patient movements.

Thus, there is a need to improve the approaches to measuring and characterizing patient motion and movement in real-time. Improving the characterization of patient motion allows for a more fulsome predictive analysis of patient actions and evaluation of patient conditions. For example, as a patient progresses out of sedation, certain motions are indicative of the state of consciousness of the patient. Also, certain motions are indicative of a patient preparing to make a movement such that monitoring for the motion provides an advanced indication that may be used to alert a caregiver that a patient is preparing to make an attempt to exit the patient support apparatus.

SUMMARY

The present disclosure includes one or more of the features recited in the appended claims and/or the following features which, alone or in any combination, may comprise patentable subject matter.

According to a first aspect of the present disclosure, a patient support apparatus comprise a first frame, a plurality of load cells positioned on the first frame, a second frame, and a control system. The second frame is supported on the load cells such that the load of the second frame is measured by the load cells, the second frame configured to support a patient supported on the patient support apparatus such that the load of the patient is transferred through the plurality of load cells. The control system includes a controller. The controller is operable to receive a separate signal from each of the plurality of load cells, process the signals to identify, based on transient changes in the forces measured by each of the plurality of load cells, motion of the patient that does not result in relative movement of the patient relative to the second frame. The motion of the patient is further processed to characterize the nature of the patient motion and, based on the characterization of the patient motion automatically update a patient profile in a patient record to reflect the characterization of the patient motion.

In some embodiments, the transient changes in the forces measured by the load cells are indicative of motion of a least a portion of the patient in a vertical direction.

In some embodiments, the controller is operable to calculate the work done by the patient in the vertical direction to characterize the patient motion.

In some embodiments, the controller is operable to calculate the work done by the patient and distinguish between motion that results in movement of the patient's mass to a different position on the patient support apparatus from motion that does not result in movement of the patient's mass to a different position on the patient support apparatus and updates the patient profile to reflect the net movement of the patient and the motion that does not result in movement of the patient's mass to a different position on the patient support apparatus.

In some embodiments, the controller is operable to calculate a speed of movement of the center of gravity of the patient in the plane that is orthogonal to the direction of gravity to determine the amount of work done by the patient moving in the plane that is orthogonal to the direction of gravity.

In some embodiments, the controller is operable to calculate the work done by a patient that does not result in movement in the plane that is orthogonal to the direction of gravity.

In some embodiments, the controller is operable to determine the work that is done to move the patient in the direction of gravity and the work that is done to move the patient in the plane that is orthogonal to the direction of gravity and updates the patient profile based on the total work done by the patient.

In some embodiments, the controller is operable to distinguish between patient motion and non-patient motion artifacts and disregards non-patient motion artifacts when updating the patient profile.

In some embodiments, the controller is operable to determine the existence of a non-patient motion artifact by closed system analysis that detects that an additional load has been added to the load cells.

In some embodiments, the additional load is determined using an analysis of the sum of the values detected by the load cells to determine if the net load of the load cells has been affected by an external input.

According to a second aspect of the present disclosure, patient support apparatus comprises a plurality of load cells, a frame supported on the load cells such that the load of the frame is measured by the load cells, the frame configured to support a patient supported on the patient support apparatus such that the load of the patient is transferred through the plurality of load cells, and a control system. The control system includes a controller. The controller is operable to receive a separate signal from each of the plurality of load cells, process the signals to identify, based on transient changes in the forces measured by each of the plurality of load cells, motion of the patient. The controller is operable to classify the motion of the patient, and, based on the classification, update a patient profile in a patient record to reflect the characterization of the patient motion.

In some embodiments, the transient changes in the forces measured by the load cells are indicative of motion of a least a portion of the patient in a vertical direction.

In some embodiments, the controller is operable to calculate the work done by the patient in the vertical direction to characterize the patient motion.

In some embodiments, the controller is operable to calculate the work done by the patient and distinguish between motion that results in movement of the patient's mass to a different position on the patient support apparatus from motion that does not result in movement of the patient's mass to a different position on the patient support apparatus and updates the patient profile to reflect the net movement of the patient and the motion that does not result in movement of the patient's mass to a different position on the patient support apparatus.

In some embodiments, the controller is operable to calculate a speed of movement of the center of gravity of the patient in the plane that is orthogonal to the direction of gravity to further determine the amount of work done by the patient moving in the plane that is orthogonal to the direction of gravity.

In some embodiments, the controller is operable to calculate the work done by a patient that does not result in movement in the plane that is orthogonal to the direction of gravity.

In some embodiments, the controller is operable to determine the work that is done to move the patient in the direction of gravity and the work that is done to move the patient in the plane that is orthogonal to the direction of gravity and updates the patient profile to reflect the total work done by the patient.

In some embodiments, the controller is operable to distinguish between patient motion and non-patient motion artifacts and disregards non-patient motion artifacts when updating the patient profile.

In some embodiments, the controller is operable to determine the existence of a non-patient motion artifact by closed system analysis that detects that an additional load has been added to the load cells.

In some embodiments, the additional load is determined using an analysis of the sum of the values detected by the load cells to determine if the net load of the load cells has been affected by an external input.

According to a third aspect of the present disclosure, a method of characterizing the condition of a patient supported on a patient support apparatus having a plurality of load cells that support the patient load, the method comprises receiving a separate signal from each of the plurality of load cells. The method also comprises processing the signals to identify, based on transient changes in the forces measured by each of the plurality of load cells, motion of the patient that does not result in a change of position of the patient on the patient support apparatus. The method also comprises characterizing the nature of the patient motion; and based on the characterization of the patient motion, automatically updating a patient profile in a patient record to reflect the characterization of the patient motion.

In some embodiments, the method further comprises determining, based on the transient changes in the forces measured by the load cells, the magnitude of motion of a least a portion of the patient in a vertical direction.

In some embodiments, the method further comprises calculating the work done by the patient in the vertical direction to characterize the patient motion.

In some embodiments, the method further comprises calculating the work done by the patient, distinguishing between motion that results in movement of the patient's mass to a different position on the patient support apparatus from motion that does not result in movement of the patient's mass to a different position on the patient support apparatus, and updating the patient profile to reflect the net movement of the patient and the motion that does not result in movement of the patient's mass to a different position on the patient support apparatus.

In some embodiments, the method further comprises calculating a speed of movement of the center of gravity of the patient in the plane that is orthogonal to the direction of gravity to further determine the amount of work done by the patient moving in the plane that is orthogonal to the direction of gravity.

In some embodiments, the method further comprises calculate the work done by a patient that does not result in movement in the plane that is orthogonal to the direction of gravity, and updating the patient profile to reflect the work done by the patient.

In some embodiments, the method further comprises determining the work that is done to move the patient in the direction of gravity and the work that is done to move the patient in the plane that is orthogonal to the direction of gravity, and updating the patient profile to reflect the total work done by the patient.

In some embodiments, the method further comprises distinguishing between patient motion and non-patient motion artifacts, and disregarding non-patient motion artifacts when updating the patient profile.

In some embodiments, the method further comprises determining the existence of a non-patient motion artifact by closed system analysis that detects that an additional load has been added to the load cells.

In some embodiments, the method further comprises determining the additional load using an analysis of the sum of the values detected by the load cells to determine if the net load of the load cells has been affected by an external input.

According to a fourth aspect of the present disclosure, a method of characterizing the condition of a patient supported on a patient support apparatus having a plurality of load cells that support the patient load, the patient support apparatus having a patient support surface with an x-axis, a y-axis, and a z-axis, the method comprises receive a separate signal from each of the plurality of load cells, calculating a speed of movement of the center of gravity of the patient in the plane defined by the x-axis and y-axis by using the forces measured in the x-axis and y-axis, and notifying a caregiver of a patient status based on the speed of movement.

In some embodiments, the method further comprises calculating total work done by the patient in the plane defined by the x-axis and y-axis based on the speed of movement of the center of gravity.

In some embodiments, the method further comprises calculating a speed of movement of the patient in z-axis by using the forces measured in the z-axis.

According to a fifth aspect of the present disclosure, a method of characterizing the condition of a patient supported on a patient support apparatus having a plurality of load cells that support the patient load, the patient support apparatus having a patient support surface with an x-axis, a y-axis, and a z-axis, the method comprises receiving a separate signal from each of the plurality of load cells, processing the signals to identify changes in the forces measured by each of the plurality of load cells, calculating total work done by the patient based on the changes in force, and notifying a caregiver of a patient status based on the total work done.

In some embodiments, the method further comprises calculating total work done by the patient in the plane defined by the x-axis and y-axis based on the speed of movement of the center of gravity.

In some embodiments, the method further comprises calculating a speed of movement of the patient in z-axis by using the forces measured in the z-axis.

According to as sixth aspect of the present disclosure, a method of characterizing the condition of a patient supported on a patient support apparatus having a plurality of load cells that support the patient load, the patient support apparatus having a patient support surface with an x-axis, a y-axis, and a z-axis, the method comprises receiving a separate signal from each of the plurality of load cells, processing the signals to identify any changes in forces in the x-axis, y-axis, and z-axis, calculating at least one of speed of the center of gravity, kinetic energy of the patient, and total work done by the patient, based on the changes in forces, and notifying a caregiver of a patient status based on the calculation.

In some embodiments, the method further comprises calculating total work done by the patient in the plane defined by the x-axis and y-axis based on the speed of movement of the center of gravity.

In some embodiments, the method further comprises calculating a speed of movement of the patient in z-axis by using the forces measured in the z-axis.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
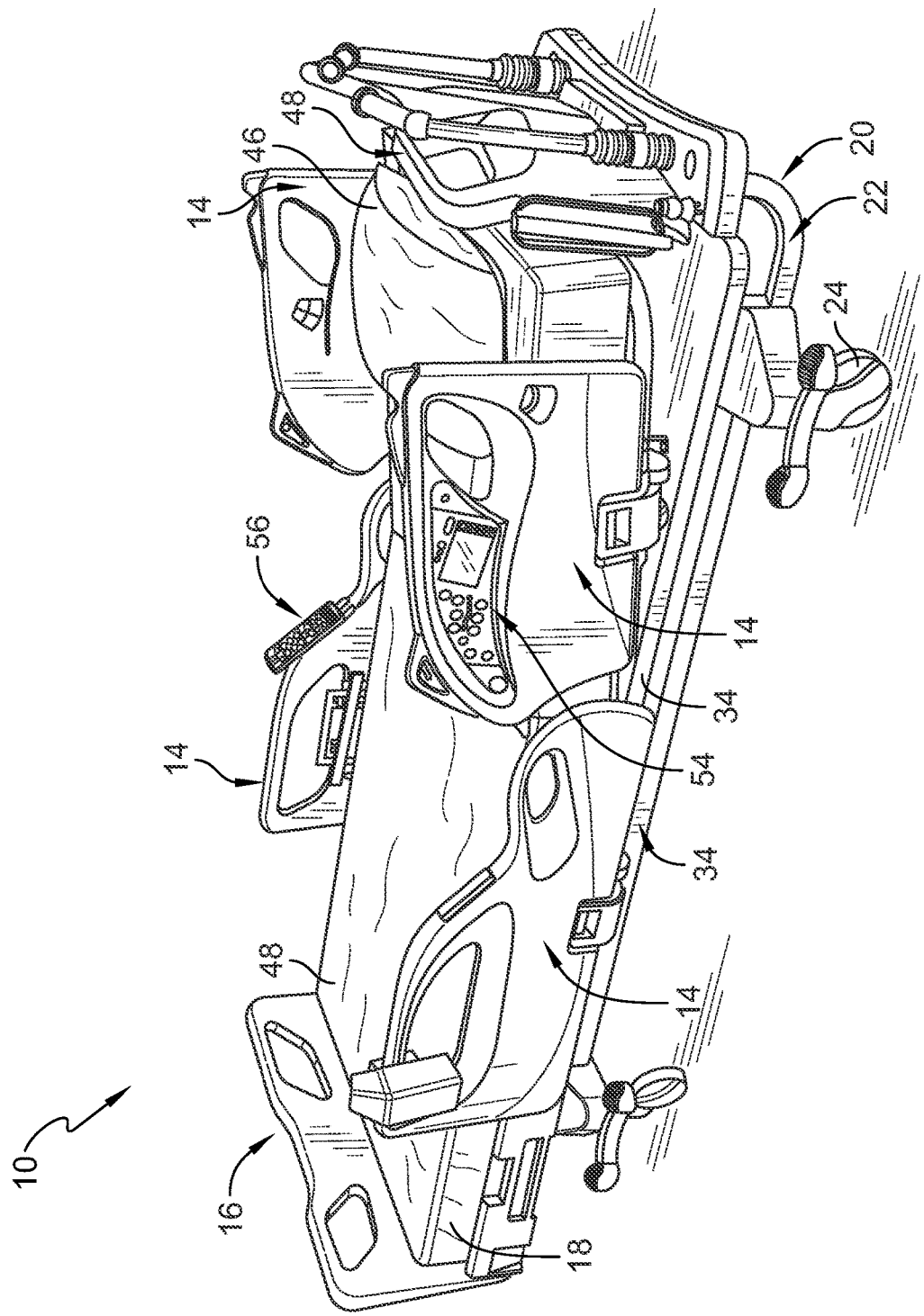
FIG. 1 is a perspective view of a patient support apparatus including a control system operable to measure signals from a plurality of sensors and process those signals according to the present disclosure.

An illustrative patient support apparatus 10 embodied as a hospital bed is shown in FIG. 1. The bed 10 of FIG. 1 has a frame 20 which includes a base frame 22 supported on casters 24. The stationary base frame 22 further supports a weigh frame 30 that an adjustably positionable mattress support upper frame 34 supporting a mattress 18. The illustrative mattress 18 is an inflatable patient support surface which includes inflatable zones including a head zone 36, a seat zone 38, thigh zone 40, and a foot zone 42. The bed 10 further includes a headboard 12 at a head end 46 of the bed 10, a footboard 16 at a foot end 48 of the bed 10, and a movable siderails 14 coupled to the upper frame 34 of the bed 10. The bed 10 also includes a user interface 54 positioned on one of the siderails 14. The bed 10 of the embodiment of FIG. 1 is conventionally configured to adjustably position the upper frame 34 relative to the base frame 22 to adjust the position of a patient supported on the mattress 18.

Conventional structures and devices may be provided to adjustably position the upper frame 34, and such conventional structures and devices may include, for example, linkages, drives, and other movement members and devices coupled between base frame 22 and the weigh frame 30, and/or between weigh frame 30 and upper frame 34. Control of the position of the upper frame 34 and mattress 18 relative to the base frame 22 or weigh frame 30 is controlled, for example, by a patient control pendant 56 or user interface 54. The upper frame 34 may, for example, be adjustably positioned in a general incline from the head end 46 to the foot end 48 or vice versa. Additionally, the upper frame 34 may be adjustably positioned such that the head section 44 of the mattress 18 is positioned between minimum and maximum incline angles, e.g., 0-65 degrees, relative to horizontal or bed flat, and the upper frame 34 may also be adjustably positioned such that a seat section (not shown) of the mattress 18 is positioned between minimum and maximum bend angles, e.g., 0-35 degrees, relative to horizontal or bed flat. Those skilled in the art will recognize that the upper frame 34 or portions thereof may be adjustably positioned in other orientations, and such other orientations are contemplated by this disclosure.

Figure 2:
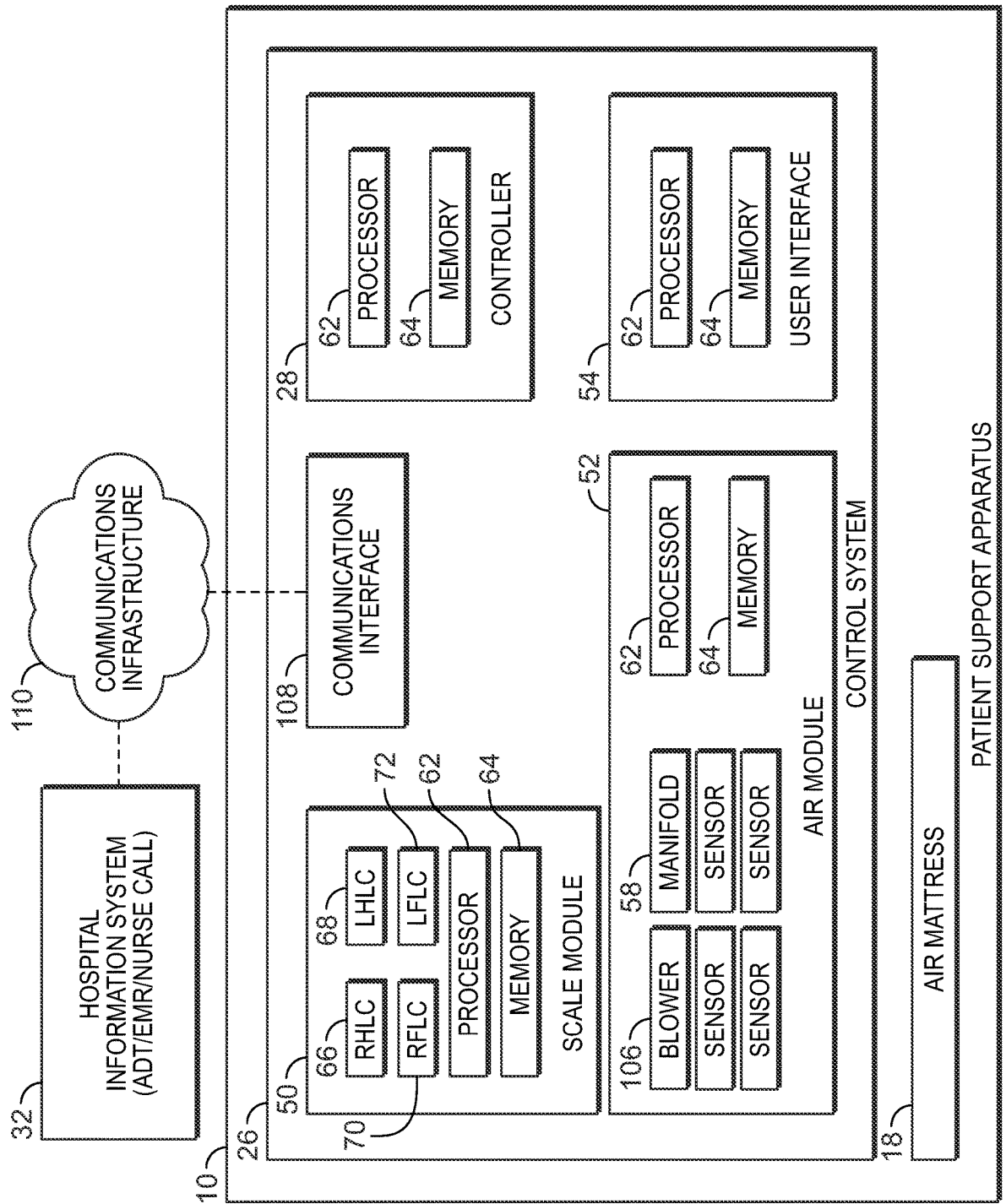
FIG. 2 is a block diagram of a portion of the control system of the patient support apparatus of FIG. 1.

In one illustrative embodiment shown diagrammatically in FIG. 2, the bed 10 has a control system 26 that includes a controller 28, a scale module 50, an air module 52, and the user interface 54. In the illustrative embodiment each of the controller 28, scale module 50, air module 52, and user interface 54 includes a processor 62 and a memory device 64. The processor 62 and memory device 64 are shown only with respect to the controller 28, but similar structures are used in the scale module 50, air module 52, and user interface 54. The memory device 64 includes instructions that, when executed by the processor 62, cause the processor 62 to perform functions as associated with the particular one of controller 28, scale module 50, air module 52, and user interface 54. The components of the control system 26 communicate amongst themselves to share information and distribute the functions of the bed 10. The processor 62 of each of the controller 28, scale module 50, air module 52, and user interface 54 is also operable, based on instructions from the memory device 64, to communicate with the others of the controller 28, scale module 50, air module 52, and user interface 54 using a communications protocol. It should be understood that the term processor here includes any microprocessor, microcontroller, processor circuitry, control circuitry, preprogrammed device, or any structure capable of accessing the memory device and executing non-transient instructions to perform the tasks, algorithm, and processed disclosed herein. In the illustrative embodiment, the control system 26 employs a conventional controller area network (CAN) for communications between subsystems, but it should be understood that any of a number of networking and communications solutions could be employed in the control system 26.

Figure 3:
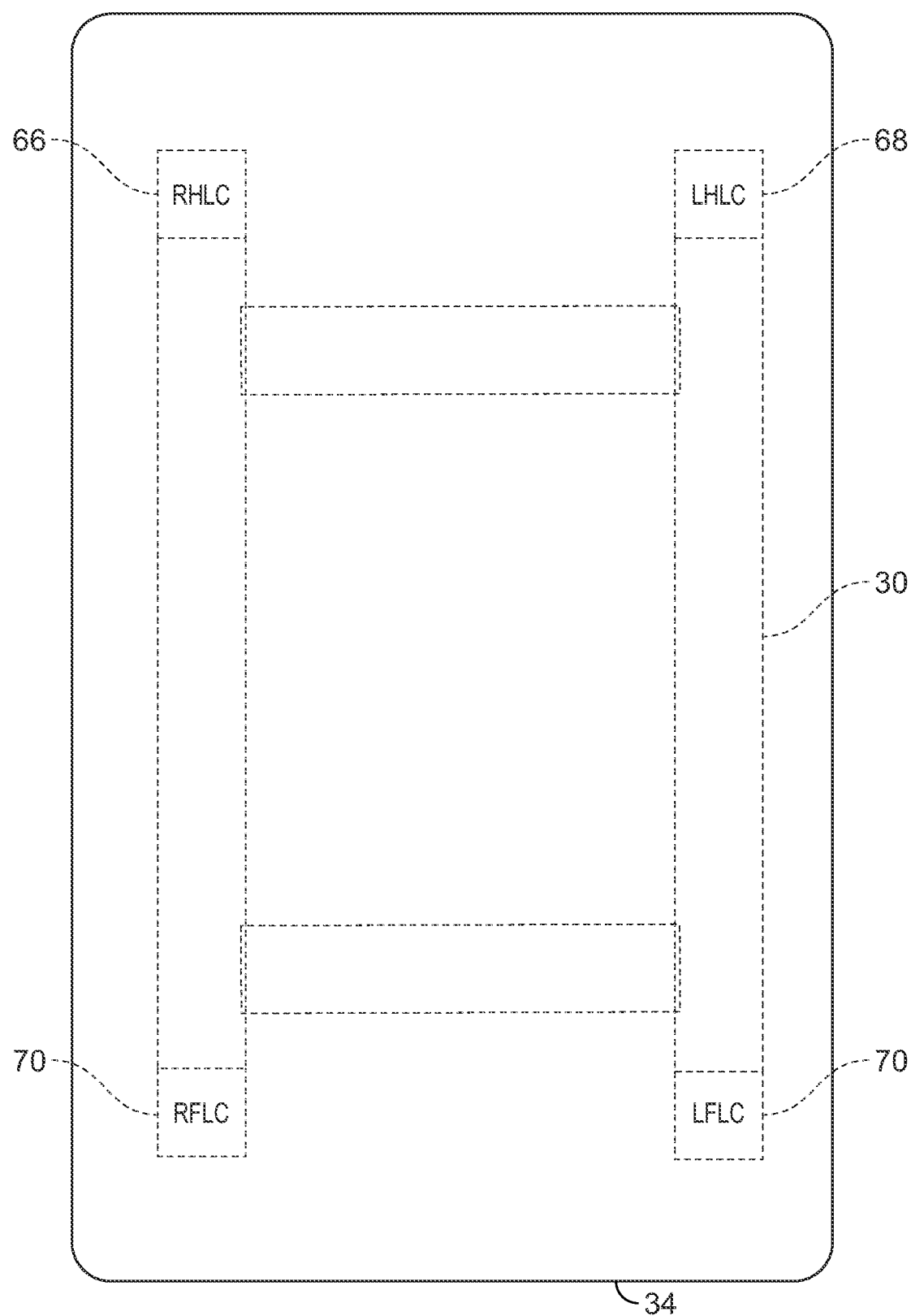
FIG. 3 is a diagrammatic illustration of the interaction between a first frame of the patient support apparatus of FIG. 1 and a second frame supported on load cells supported from the first frame.
Figure 4:
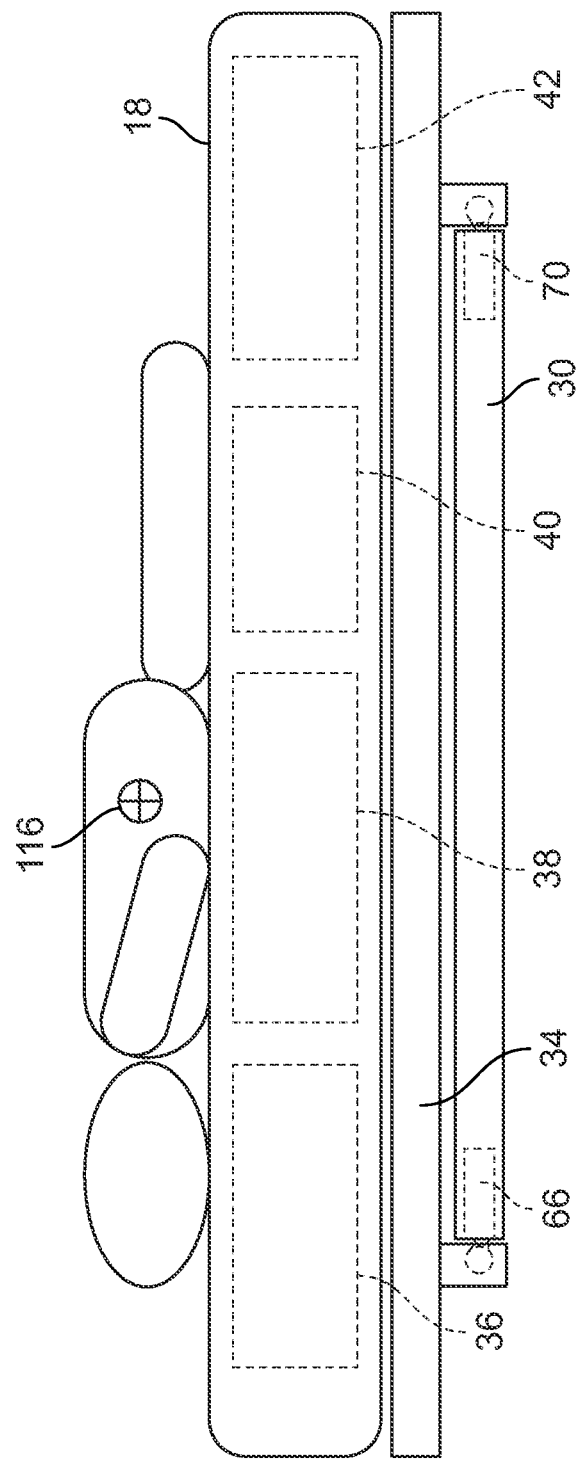
FIG. 4, is a side view of a portion of the patient support apparatus of FIG. 1 showing a first frame supported on load cells supported on a second frame, the load cells supporting all of the load of the first frame.
Figure 5:
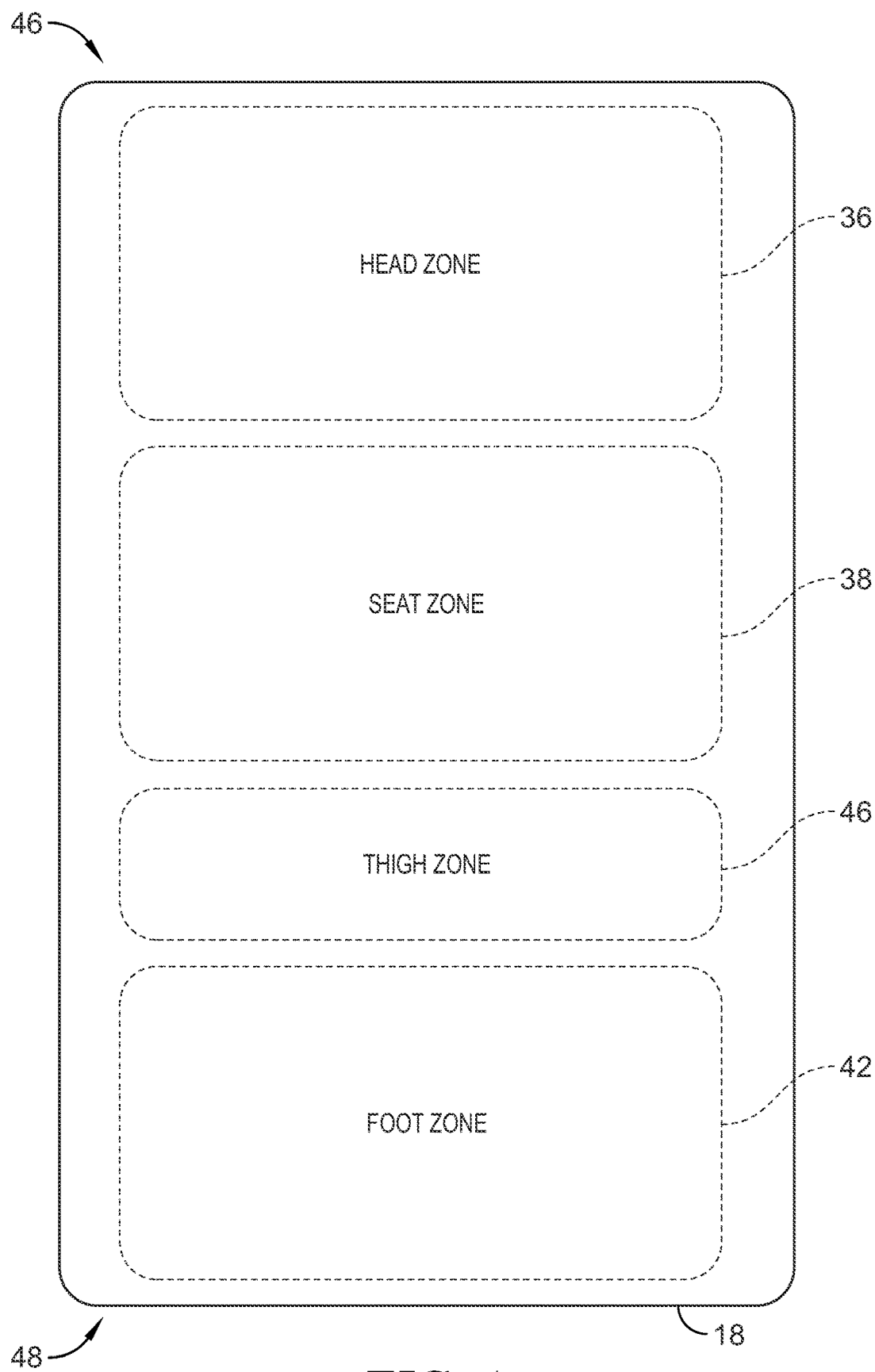
FIG. 5 is a diagrammatic representation of a mattress of the patient support apparatus of FIG. 1, the mattress including multiple inflatable zones.

The scale module 50 includes four load cells 66, 68, 70, and 72. To determine a weight of a patient supported on the mattress 18, the load cells 66, 68, 70, and 72 are positioned between the weigh frame 30 and the upper frame 34 as illustrated in FIGS. 3 and 4. Each load cell 66, 68, 70, 72 is configured to produce a signal indicative of a load supported by the respective load cell 66, 68, 70, 72 from the upper frame 34 relative to the weigh frame 30. Some of the structural components of the bed 10 will be designated hereinafter as "right", "left", "head" and "foot" from the reference point of an individual lying on the individual's back on the mattress 18 with the individual's head oriented toward the head end 46 of the bed 10 and the individual's feet oriented toward the foot end 48 of the bed 10. Following this convention, the load cell 66 is designated as the right head load cell (RHLC) in the figures to represent that the load cell 66 is positioned at the right side of the bed 10 at the head end 46. The load cell 68 is designated at the left head load cell (LHLC), the load cell 70 is designated as the right foot load cell (RFLC), and the load cell is designated left foot load cell (LFLC), each following the same convention.

The scale module 50 includes a processor 62 that is in communication with each of the respective load cells 66, 68, 70, and 72 and operable to process the signals from the load cells 66, 68, 70, and 72. The memory device 64 is also utilized by the controller 28 to store information corresponding to features and functions provided by the bed 10.

A weight distribution of a load among the plurality of load cells 66, 68, 70, and 72 may not be the same depending on variations in the structure of the bed 10, variations in each of load cells 66, 68, 70, and 72 and the position of the load on the mattress 18 relative to the particular load cell 66, 68, 70, or 72. Accordingly, a calibration constant for each of the load cells 66, 68, 70, and 72 is established to adjust for differences in the load cells 66, 68, 70, and 72 in response to the load borne by each. Each of the load cells 66, 68, 70, and 72 produces a signal indicative of the load supported by that load cell 66, 68, 70, or 72. The loads detected by each of the respective load cells 66, 68, 70, 72 are adjusted using a corresponding calibration constant for the respective load cell 66, 68, 70, 72. The adjusted loads are then combined to establish the actual weight supported on the bed 10. In the present disclosure, the independent signals from each of the load cells 66, 68, 70, 72 is used to draw inferences about the movement and motion of the patient.

The air module 52 is the functional controller for the mattress 18 and includes processor 62 and a memory device 64. The processor 62 is in communication with a blower 106, a manifold 58, and an air pressure sensor assembly 60. The air module 52 is a conventional structure with the manifold 58 operating under the control of the processor 62 to control the flow of air from the blower 106 into and out of the head zone 36, seat zone 38, thigh zone 40, and foot zone 42 to control the interface pressure experienced by the patient supported on the mattress 18. However, the present disclosure is directed to using the information from sensor assembly 60 to make further inferences regarding motion by the patient supported on the mattress 18. The sensor assembly 60 includes separate sensors for measuring the air pressure in each of the head zone 36, seat zone 38, thigh zone 40, and foot zone 42. The pressure sensor assembly includes a head zone sensor 82, a seat zone sensor 84, a thigh zone senor 86, and a foot zone sensor 88. While signals from the sensors 82, 84, 86, and 88 are used to control the pressure in the respective zones, applying the principles of the present disclosure, the signals are also useful in making inferences regarding patient movement and, when used synergistically with the information gleaned from the signals from the load cells 66, 68, 70, and 72, provide a more fulsome and accurate analysis of patient movement and/or motion.

Figure 6:
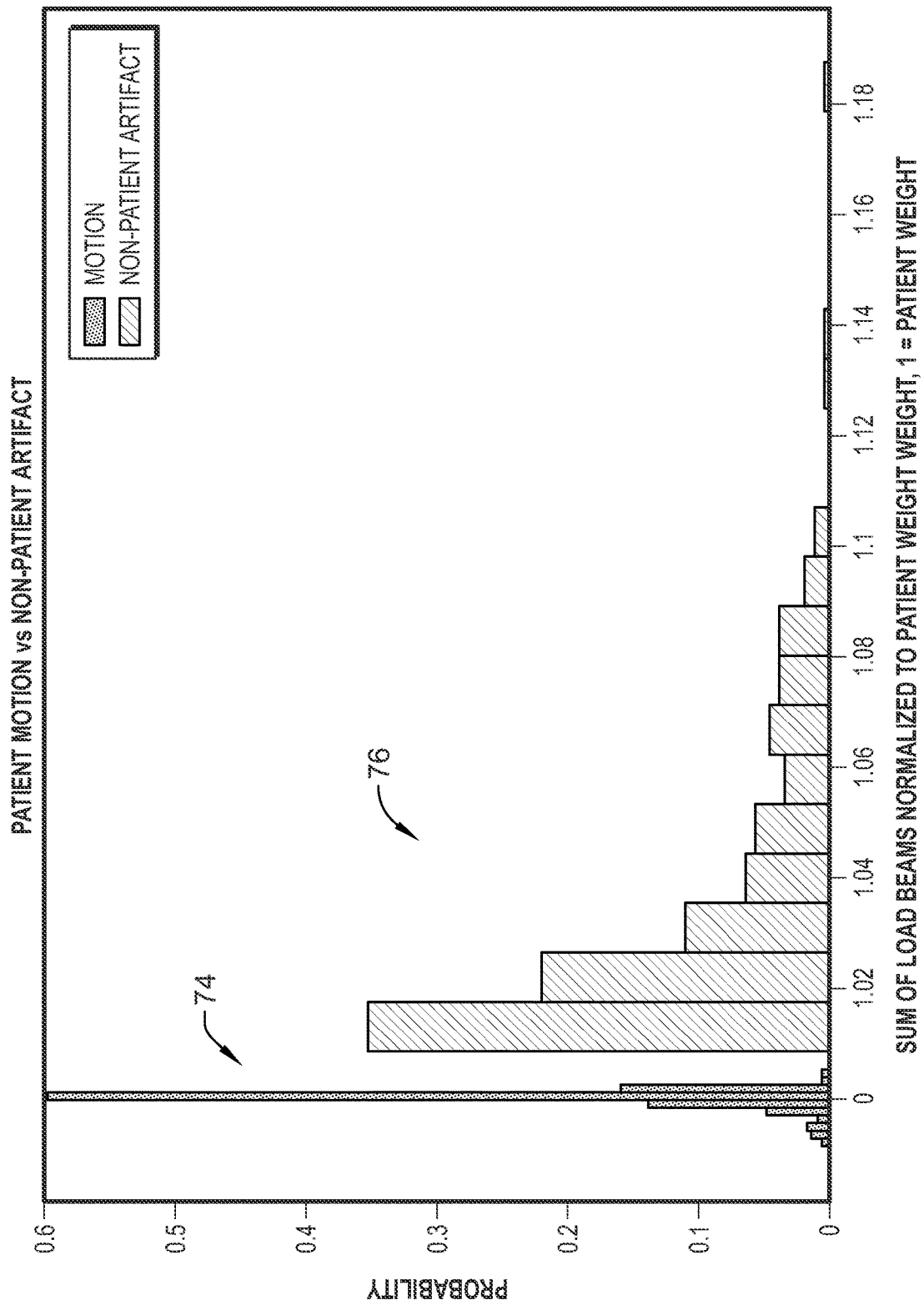
FIG. 6 is a graphical representation of a group of data collected from the patient support apparatus of FIG. 1, the graphical representation showing the difference between incidents of patient movement detected by the sensors of the patient support apparatus and non-patient movement artifacts detected by the sensors.

Thus, the present disclosure is directed to utilizing the bed 10, and specifically the scale module 50 and air module 52, as an instrument for measuring the motions of a patient that occupies the bed 10 and characterizing that motion to make inferences about the patient's health. Like all biomedical sensing systems, error can be introduced when the sensor output is affected by various sources of noise. Some sources of noise, such as electrical or stray environmental noise can be mitigated through robust design. However, it is not always possible to mitigate human-caused forces that are imparted to the load cells 66, 68, 70, and 72 that are not generated from solely the patient themselves. These artifacts are referred to herein as non-patient motion artifacts (NPMA). FIG. 6 is a graph demonstrating the relationship between strictly patient motions, shown as narrow columns at reference 74, to NPMAs, shown as wide columns at reference 76. When NPMAs occur, they are typically much greater in motion magnitude than patient motions. Failure to acknowledge and adjust for the presence of these NPMA results in an inaccurate inference of mobility, self-directed motion, etc. to bias towards patients having much more mobility than they actually have.

Figure 7:
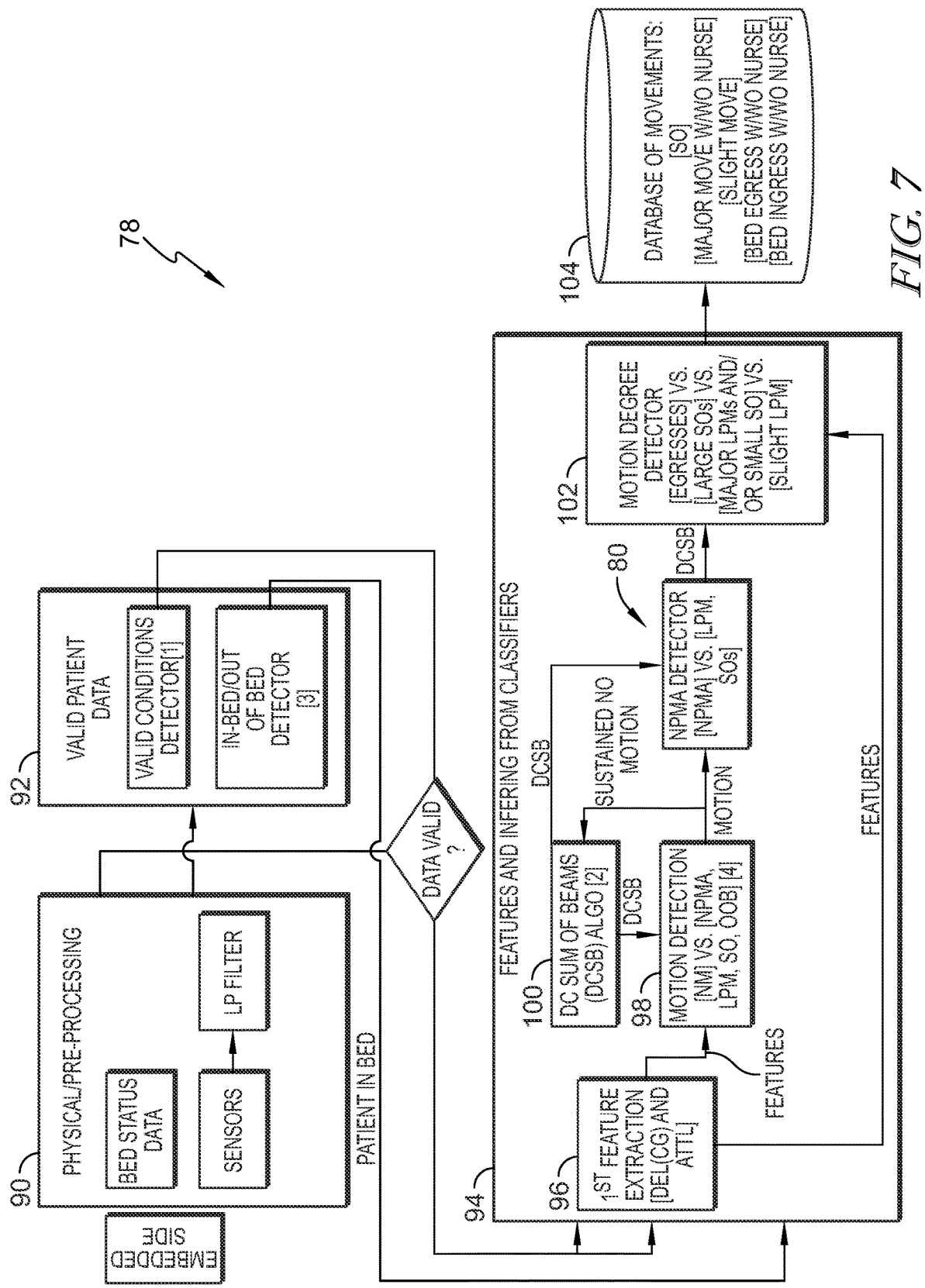
FIG. 7 is a diagrammatic representation of an algorithm for characterizing sensor signals from the patient apparatus of FIG. 1.

The present disclosure is directed to having a practical and accurate analysis and mitigation of NPMAs in real-time. Once determined, load cell signal data that has aspects of NPMA movement can be mitigated or ignored such that true-patient motion can be determined. Referring now to FIG. 7, an algorithm 78 for true motion detection is illustrated, including the NPMA detector function 80.

Through an empirical study that included real-time data collection from video observation of test subject patients synchronized with signals from load cells of the scale module of the bed supporting the test subject patients, the types of motion from the where classified in one of three types: lateral patient motions (LPMs); vertical or self-offloading patient movements (SOs); or non-patient motion artifacts (NPMAs). There were also observations that found that load cell signals varied when there was no patient movement. These artifacts were designated as non-movements (NMs). Permutations of these categories, called "complex movements", also including further categorization into combinations including different directionality of the simple movements was also established.

The use of the signals from the load cells of a bed, such as load cells 66, 68, 70, and 72 to determine the equivalent centroid of vertical load supported by the load cells 66, 68, 70, and 72 is known. This centroid/center-of-gravity (CG) approach is used to infer some patient motion. Through empirical analysis, a determination of motion in the x/y plane (see FIG. 1) of a range of speeds and magnitudes of motion that are associated with patient motions has been determined. Thus, this allows for the detection of lateral patient motions (LPMs), which are, by definition, detected patient motions which have no vertical component. Any lateral movement will cause the center of gravity of the bed to change during a unit-time interval, proportionally to ratio of the displacement of the amount of mass moved to the amount of mass that remained stationary. Due to this, this feature is self-normalized by patient weight. Note that CG movement in the x and y axis is merged by typical vector addition and the directionality is ignored to establish a factor called CGspeed. It is understood that both patient and non-patient movements will cause the CG to move, for these reasons, and the classifiers and inference models discussed below, any motion that imparts its force to the weigh frame 30 is considered to be a motion.

In a first approach at discriminating NPMAs from LPMs, the patient and the bed 10 are treated as a closed system. The total energy of the closed system will be constant and conserved over time of typical patient movements. Any energy that is created by the patient as a result of them moving does not change the overall loading of all four load cells 66, 68, 70, and 72, but simply changes the proportion the total load that each load cell 66, 68, 70, or 72 is carrying at any given time. There is no total gain of loads, the loads simply shift around the four load cells 66, 68, 70, and 72 as the patient moves laterally.

In contrast, when a caregiver pushes or pulls on the patient or bed 10 (a NPMA), the closed-system is corrupted by an external energy source and the net load on the load cells 66, 68, 70, and 72 increased or decreased. This is the case for both transient touches of the bed 10, such as when a person hugs the patient, and in sustained touches of the bed 10, such as when a caregiver leans on bed 10 while doing long procedure. In either case, an additional load is introduced to the load cells 66, 68, 70, and 72 resulting in a material change from the sum of the loads on each load cell 66, 68, 70, and 72 when the transient load is applied to the bed 10. The value of the transient load, designated as total transient load (TTL) is calculated by subtracting the from the total load measured by the load cells 66, 68, 70, and 72 the closed-system load measured before the transient event; the closed-system load which is effectively the patient's static weight, designated as the DC sum of beams (DCSB) which can be determined using known techniques, such as that disclosed in U.S. Pat. No. 10,054,479 titled "BED WITH AUTOMATIC WEIGHT OFFSET DETECTION AND MODIFICATION," which is incorporated herein for the disclosure of monitoring and updating a patient load to establish a static patient weight, DCSB.

Once the DCSB is established, a simple threshold can be tested to determine whether a TTL is a NPMA or not. The units here are forces, measured in kg, also called kg-force. As part of the test of the threshold, an oscillation in the location of the CG and an effective return of the TTL to zero can be considered to confirm the transient nature of the load to help confirm that the event is a TTL.

However, there is an exception to this simple approach. Relying just on thresholding TTL moment-by-moment is confounded by self-offloading patient movements (SOs). SOs are large vertical shifts that are an artifact of a patient quickly lifting their core body up using the strength in his legs or arms and then returning to a starting or near starting position. These self-movements cause large momentary changes in TTL and may appear to be an NPMA. Although SOs can cause momentary large shifts from the patient's weight in the closed system, appearing to break it, the closed system is not broken if the response of the system through the entire duration of the motion is considered.

Figure 8:
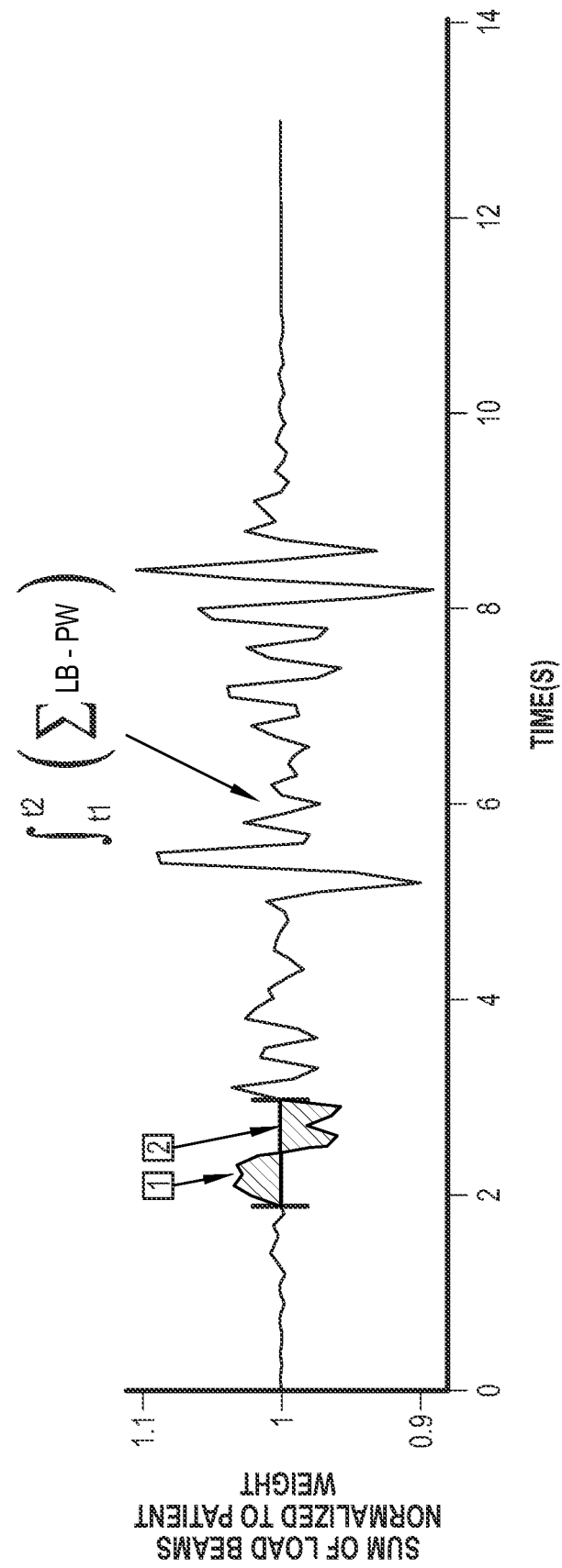
FIG. 8 is a graphical representation of a time series of a sensor signal from a group of sensor of the patient support apparatus of FIG. 1.

Referring to FIG. 8, the phenomenon of an SO event is illustrated with reference to the variation the sum of the signals from the load cells 66, 68, 70, and 72 over time. The initial forces imparted to move the trunk of the patient create a spike in the measured load as the movement begins to occur in a preload phase designated as 1 on the graph in FIG. 8. The forces oscillate after the movement occurs in a reaction phase, designated as 2 on the graph in FIG. 8. This is a result of a sort of conservation of energy. The integral or sum of TTL over this event is approximately zero when an SO event is experience, where TTL is negative at points in time, such as the designation 2. Under this conservation of energy approach, the SO is detected when any loads induced by the motion of the patient are offset by reactionary loads.

To establish characterization criteria, an empirical study using the synchronized video and load cell signal capture approach discussed above was implemented to gather a mixture of human-generated and human-surrogate test movements were performed. Taking care to vary parameters such as motion speed and magnitude of both patient and NPMA movements, and introducing variability such as different body shapes and strengths in the case of the human subjects, a representative data sample was developed. In the case of the human subjects, three subjects were used a ten-year-old male, 44.5 kg, a fourteen-year-old female, 60 kg, and a forty-year-old male, 101 kg.

Using the empirically generated test data, an approach was developed to model the absolute total transient load (ATTL), which is defined as:

$$\text{ATTL}=|[\Sigma(\text{RHLC,LHLC,RFLC,LFLC})-\text{DCSB}]/\text{DCSB}| \quad \text{(EQ. 1)}$$

Where RHLC, LHLC, RFLC, and LFLC are the values in kg, of the four load cells 66, 68, 70, and 72 and DCSB, which is defined above. This approach provides an absolute value of the TTL, recognizing that transient loads may also unload the weigh frame 30 in some situations.

The conservation of energy theory was modeled using an integral approach and taking the absolute value of the integral as shown below.

$$\text{centInt}=|\int_L^{-L}[(\text{sum(RHLC,LHLC,RFLC,LFLC)}-\text{DCSB})/\text{DCSB}]| \quad \text{(EQ. 2)}$$

A third modeling equation was derived to calculate CGspeed, which is discussed in theory above, and these equations were used:

$$CGspeed = \frac{\left(\sqrt{\Delta CGx^2 + \Delta CGy^2}\right)}{t} \quad \text{(EQ. 3)}$$

$$CGx = X * (LHLC + LFLC)/sum(RHLC, LHLC, RFLC, LFLC) \quad \text{(EQ. 4)}$$

$$CGy = Y * (RHLC + RFLC)/sum(RHLC, LHLC, RFLC, LFLC) \quad \text{(EQ. 5)}$$

Where t, is the time interval over which the change in the position of the CG moves and where X is the distance between the left load cells 68, 72 and the right load cells 66, 70, and Y is the distance between head load cells 66, 68 and the foot load cells 70, 72.

The empirically collected test data was manually annotated as patient movement (SO, LPM, or out of bed (OOB)), non-patient motion artifact (NPMA) or no-movement (NM). Patient movements occurring simultaneously with NPMAs were considered labeled as NPMAs, since ultimately it is more important to correctly identify NPMAs when they occur, potentially during patient movement, and throw out all of the data so as not to bias patient movements. To guard against human error of labeling, movements for training and validation were "moved inward", starting 0.5 seconds later and 0.5 before the end as was labeled by humans on all classes. If the (non)movement was greater than 5 seconds, 1 second was used instead of 0.5 seconds. Each feature was calculated in 100 ms intervals, which was determined to be appropriate.

Table 1 below summarizes the different classes used, the expected responses of the features, and the labeling of the response variables used for training for machine learning. As seen in the table, the features discussed differentiate between the different categories and thus a classifier can be built with them.

TABLE 1

| Simple/complex | Type of motion | Motion Class | NPMA Class | Predictor ATTL | Predictor centInt | Predictor CGspeed |
|---|---|---|---|---|---|---|
| — | Nomotion (NM) | 0 | 0 | low | low | low |
| simple | LPM | 1 | 0 | low | low | high |
| simple | SO | 1 | 0 | high | high | high |
| simple | NPMA | 1 | 1 | high | low | high |
| complex | LPM_OOB | 1 | 0 | varies | varies | high |
| complex | LPM_NPMA | 1 | 1 | varies | varies | high |

Data was visualized to confirm the theoretical behavior suspected, as laid out in Table 1. Although it appears that patient motion is predicted by one variable, and NPMA/non-NPMA is determined by two, an approach that would serialize classifiers by determining if there is ANY motion (patient or non-patient) and pass that data into the classifier that determines the presence of NPMA vs. non NPMA was implemented.

A binary logistic regression was used to determine a simple threshold that could easily be deployed in an embedded system. A 10-times K-folds cross-validation with an 80/20 ratio split of the training from the validation data was performed. An AUC-ROC curve was prepared to score the performance of the motion classifier classification approach applied at various thresholds for TPR vs. FPR. The validation test resulted in an ROC AUC of 0.99, which is a near-perfect classifier. For this motion detection model, using a threshold of 0.5, 94% of the time true motion is detected and 99% of the time true no motion is detected.

The coefficients from the empirical model describes the size and direction of the relationship between a predictor feature and the response variables. Using the dataset, the estimated coefficient for the center of gravity speed is −24.43 and change in absolute changes in transient load (ATTL) is −14.57. The intercept of this model is 4.98. Using these coefficients, the following relationship describes motion or no motion:

$$\ln\frac{Pm}{(1-Pm)} = \beta_1 + x_2\beta_2 + x_1\beta_1 + = 14.98 - 24.43*CGspeed - 14.57*ATTL \quad (EQ.\ 6)$$

Where Pm is the probability there is a motion.

Due to the binary shape of a sigmoid (shape that is used in logistic regression), this equation represents a line in a two-dimensional feature space, where it can be said that any data point above this line will be motion and any data point below this line will be no-motion group.

The data was further analyzed with a single factor to test for NPMA events and an estimated threshold coefficient for centInt was 2.87 and the intercept was −4.95. The following equation represents a vertical line indicating that any data point to the right side will be NPMA.

$$\ln\frac{Pn}{(1-Pn)} = \beta_0 + x_1\beta_1 = -4.95 + 2.87*(intCent) \quad (EQ.\ 7)$$

Where Pn is the probability there is a NPMA event.

Having successfully established that the features under study could be extracted and applied with confidence in an inference model, a generalized algorithm 78 for processing sensor data from existing sensors from a bed 10 was developed as shown in FIG. 7. At a pre-processing step 90, bed status data and sensor data are pre-processed with sensor data being filtered, such as through low-pass filter. Additional testing is confirmed at step 92 where data being transferred into an inference engine 94 is validated. At step 92, validation include a determination that sensor data being received is consistent with the environment of the bed and patient. In some examples, information may be received from a hospital information system 32 which indicates an expected sensor signal range. For example, validation may test the DCSB against the weight of the patient in the hospital information system 32 to validate that the signals from the load cells 66, 68, 70, 72 are reasonable. The hospital information system 32 may include an admission/discharge/transfer (ADT) management system, an electronic medical records system, or a nurse call system. Each of these units of the hospital information system 32 may regularly communicate with others of the systems or may be stand-alone systems. The validation step 92 may also use other sensors to confirm that a patient is in the bed 10 and generating meaningful data to confirm the validity of the algorithm 78 in real time.

The filtered data is provided to the inference engine 94 where at step 96 a first feature extraction is conducted. From the example above, a first feature is extracted to confirm whether there is a threshold state, such as motion or no motion. The CGspeed and ATTL analysis were each proven to be a useful to establish the presence of motion or no motion. In other embodiments, other first features may extracted as the first step in a serial classification approach. Upon extraction of the first feature, the serial classification approach is continued with the features extracted in step 96 advanced to step 98 where baseline data is tested against an extracted first feature to determine whether a threshold has been met that is indicative of motion. If no motion is detected, the algorithm 78 loops at step 98 until motion is identified and classification can be conducted.

Once motion is identified at step 98, the motion is discriminated at step 80 between NPMA and patient motion of either LPM or SO. If NPMA is identified at step 80, then the signal data is disregarded. However, confirmation and characterization of LPM or SO at step 80 is further analyzed at step 102 to establish a degree of motion. At step 102, in the illustrative embodiment, the motion can be distinguished between an egress, a large self-offloading patient movement (SO), a major lateral patient motion (LPM) and/or a small self-offloading patient movement (SO), or a slight lateral patient motion. Once the inference as to the type of patient motion is complete at step 102, the information is then moved to a database associated with the patient as step 104. For example, at step 104 the patient's medical record can be updated, based on the inference identify, objectively, the patient's motion and behavior such as regular self-offloading patient movement (SO), major lateral patient motions (LPMs), slight LPMs, or ingress or egress with or without caregiver assistance.

In addition to simple characterization of the patient motion, between an LPM, SO, egress, or ingress, the data from the load cells 66, 68, 70, 72 may be processed further to provide a higher level of sensitivity to the characterization of the patient movement. While the discussion above addresses the inference and first characterization of the patient motion, by calculating the work done by the patient during the motion, a more fulsome understanding the magnitude of the patient motion can be used to monitor the patient and provide insights as to the patient's medical progression, whether it be positive or negative.

Using Equation 3 above to calculate the CGspeed in the X-Y plane can be further processed to calculate the kinetic energy, designated "KE" by the equation:

$$KE = \tfrac{1}{2}mv^2 \tag{EQ. 8}$$

Thus, applying the known information, KE can be calculated as:

$$KE_{xy} = \tfrac{1}{2} DCSB_{mass} * CGspeed^2 \tag{EQ. 9}$$

Where DCSB is expressed as a mass. By summing the KE over the entire interval of movement by the patient, we can calculate the work the patient does in moving the X-Y plane.

$$Work_{xy} = \Sigma_{te}^{to} \Delta KE|_{t(n-1)}^{t(n)} \tag{EQ. 10}$$

To calculate the work that is done in the vertical direction, z, the approach is very similar. We calculate KE by integrating the positive half of the curve shown in FIG. 8. We only integrate the upper half of the curve, above the DCSB because the other half of the curve are the reactionary loads that are a response to the work done by the patient to bring the closed-system back to equilibrium. Thus, the calculation of KE in the z-axis is:

$$KE_z = \tfrac{1}{2} (\smallint ATTL\, dt)^2 \tag{EQ. 11}$$

Where ATTL is calculated in Equation 1 above.

$$Work_z = \Sigma_{te}^{to} \Delta KEz|_{t(n-1)}^{t(n)} \tag{EQ. 12}$$

Having calculated work in all three axes, the total work done by the patient in the movement is simply the sum:

$$Work_{total} = Work_{xy} + Work_z \tag{EQ. 13}$$

This calculation of total work with each characterized motion allows an inference as to the health of the patient. If the patient is doing less work in a given time, it is possible to infer that the patient's health has deteriorated as they are not as active. This measurement of work is provides a method of making a second order analysis of patient activity, independent of the patient's actual movement relative to the bed 10. A patient may cause motion of their body, in the z-axis, for example, without causing actual displacement of their center of gravity relative to the bed 10. In traditional models, this lack of movement would infer the patient to be immobile. Applying the principle of work in multiple dimensions, there is an ability to better characterize the patient's health.

With this in mind, we return to the control system 26 shown in FIG. 2. The control system 26 further includes a communications interface 108 that is operable, under the control of the controller 28, to communicate with the hospital information system 32 through a communications infrastructure 110 to share the patient health characterization, whether that be a mobility score, an activity score, a consciousness score, or any other objective score based on the output from the bed 10 acting as a sensor to objectively measure the work done by the patient and characterizing the type of motions patient is making.

Still further, it is contemplated that if the controller 28 detects an adverse condition, the controller 28 may communicate that adverse condition through the communications interface 108 to the hospital information system 32 for action by caregivers. Similarly, the controller 28 may communicate an adverse event to the user interface 54 which may issue an audible or visual alert of the adverse condition. The adverse condition may be based on an acceptable threshold of motion or work. In addition, the adverse condition evaluation may rely solely on a rate of change of patient motion or work. For example, a significant drop in the motion of or work being done by a patient may be an indicator of the deterioration of a patient due to, for example, sepsis, delirium, or a loss of consciousness.

Although this disclosure refers to specific embodiments, it will be understood by those skilled in the art that various changes in form and detail may be made without departing from the subject matter set forth in the accompanying claims.

The invention claimed is:

1. A patient support apparatus comprising
  a first frame,
  a plurality of load cells positioned on the first frame,
  a second frame supported on the load cells such that the load of the second frame is measured by the load cells, the second frame configured to support a patient supported on the patient support apparatus such that the load of the patient is transferred through the plurality of load cells,
  a control system including a controller, the controller operable to receive a separate signal from each of the plurality of load cells, process the signals to identify, based on transient changes in the forces measured by each of the plurality of load cells, motion of the patient that does not result in relative movement of the patient relative to the second frame, the motion of the patient being further processed to characterize the nature of the patient motion and, based on the characterization of the patient motion automatically update a patient profile in a patient record to reflect the characterization of the patient motion,
  wherein the transient changes in the forces measured by the load cells are indicative of motion of a least a portion of the patient in a vertical direction, and
  wherein the controller is operable to calculate the work done by the patient in the vertical direction to characterize the patient motion.

2. The patient support apparatus of claim 1, wherein the control system further includes a communications interface operable to communicate with a hospital information system through a communications infrastructure to share the patient health characterization.

3. The patient support apparatus of claim 1, wherein the controller is operable to detect an adverse condition of the patient based on an acceptable threshold of motion or work done by the patient, and wherein the control system further includes a communications interface operable to communicate with a hospital information system through a communications infrastructure to share the adverse condition of the patient.

4. The patient support apparatus of claim 1, wherein the controller is operable to calculate the work done by the patient and distinguish between motion that results in movement of the patient's mass to a different position on the patient support apparatus from motion that does not result in movement of the patient's mass to a different position on the patient support apparatus and updates the patient profile to reflect the net movement of the patient and the motion that does not result in movement of the patient's mass to a different position on the patient support apparatus.

5. The patient support apparatus of claim 1, wherein the controller is operable to calculate a speed of movement of the center of gravity of the patient in the plane that is orthogonal to the direction of gravity to determine the amount of work done by the patient moving in the plane that is orthogonal to the direction of gravity.

6. The patient support apparatus of claim 5, wherein the controller is operable to calculate the work done by a patient that does not result in movement in the plane that is orthogonal to the direction of gravity.

7. The patient support apparatus of claim 6, wherein the controller is operable to determine the work that is done to move the patient in the direction of gravity and the work that is done to move the patient in the plane that is orthogonal to the direction of gravity and updates the patient profile based on the total work done by the patient.

8. The patient support apparatus of claim 1, wherein the controller is operable to distinguish between patient motion and non-patient motion artifacts and disregards non-patient motion artifacts when updating the patient profile.

9. The patient support apparatus of claim 8, wherein the controller is operable to determine the existence of a non-patient motion artifact by closed system analysis that detects that an additional load has been added to the load cells.

10. The patient support apparatus of claim 9, wherein the additional load is determined using an analysis of the sum of the values detected by the load cells to determine if the net load of the load cells has been affected by an external input.

11. A patient support apparatus comprising
a plurality of load cells,
a frame supported on the load cells such that the load of the frame is measured by the load cells, the frame configured to support a patient supported on the patient support apparatus such that the load of the patient is transferred through the plurality of load cells,
a control system including a controller, the controller operable to receive a separate signal from each of the plurality of load cells, process the signals to identify, based on transient changes in the forces measured by each of the plurality of load cells, motion of the patient, classify the motion of the patient, and, based on the classification, update a patient profile in a patient record to reflect the characterization of the patient motion,
wherein the transient changes in the forces measured by the load cells are indicative of motion of a least a portion of the patient in a vertical direction, and
wherein the controller is operable to calculate the work done by the patient in the vertical direction to characterize the patient motion.

12. The patient support apparatus of claim 11, wherein the control system further includes a communications interface operable to communicate with a hospital information system through a communications infrastructure to share the patient health characterization.

13. The patient support apparatus of claim 11, wherein the controller is operable to detect an adverse condition of the patient based on an acceptable threshold of motion or work done by the patient, and wherein the controller is operable to communicate the adverse condition to a user interface of the control system, the user interface being operable to issue an audible or visual alert of the adverse condition.

14. The patient support apparatus of claim 11, wherein the controller is operable to calculate the work done by the patient and distinguish between motion that results in movement of the patient's mass to a different position on the patient support apparatus from motion that does not result in movement of the patient's mass to a different position on the patient support apparatus and updates the patient profile to reflect the net movement of the patient and the motion that does not result in movement of the patient's mass to a different position on the patient support apparatus.

15. The patient support apparatus of claim 11, wherein the controller is operable to calculate a speed of movement of the center of gravity of the patient in the plane that is orthogonal to the direction of gravity to further determine the amount of work done by the patient moving in the plane that is orthogonal to the direction of gravity.

16. The patient support apparatus of claim 15, wherein the controller is operable to calculate the work done by a patient that does not result in movement in the plane that is orthogonal to the direction of gravity.

17. The patient support apparatus of claim 16, wherein the controller is operable to determine the work that is done to move the patient in the direction of gravity and the work that is done to move the patient in the plane that is orthogonal to the direction of gravity and updates the patient profile to reflect the total work done by the patient.

18. The patient support apparatus of claim 17, wherein the controller is operable to distinguish between patient motion and non-patient motion artifacts and disregards non-patient motion artifacts when updating the patient profile.

19. The patient support apparatus of claim 18, wherein the controller is operable to determine the existence of a non-patient motion artifact by closed system analysis that detects that an additional load has been added to the load cells.

20. The patient support apparatus of claim 19, wherein the additional load is determined using an analysis of the sum of the values detected by the load cells to determine if the net load of the load cells has been affected by an external input.

* * * * *